(12) United States Patent
Flockerzi

(10) Patent No.: US 6,306,869 B1
(45) Date of Patent: Oct. 23, 2001

(54) N-OXIDES

(75) Inventor: Dieter Flockerzi, Allensbach (DE)

(73) Assignee: Byk Gulden Lomberg Chemische Febrik GmbH, Constance (DE)

( * ) Notice: Subject to any disclaimer, the term of this patent is extended or adjusted under 35 U.S.C. 154(b) by 0 days.

(21) Appl. No.: 09/673,649

(22) PCT Filed: Apr. 27, 1999

(86) PCT No.: PCT/EP99/02827

§ 371 Date: Nov. 1, 2000

§ 102(e) Date: Nov. 1, 2000

(87) PCT Pub. No.: WO99/57118

PCT Pub. Date: Nov. 11, 1999

(30) Foreign Application Priority Data

May 5, 1998 (EP) .................................................. 98108124

(51) Int. Cl.⁷ .......................... C07D 471/04; A61P 17/06; A61P 11/06; A61K 31/4375

(52) U.S. Cl. ........................... 514/287; 514/292; 546/65; 546/81

(58) Field of Search ..................... 546/81, 65; 514/287, 514/292

(56) References Cited

U.S. PATENT DOCUMENTS 6,008,215  12/1999  Flockerzi ............................ 514/212

FOREIGN PATENT DOCUMENTS 0 247 971 A  * 12/1997  (EP) .

* cited by examiner

*Primary Examiner*—Mark L Berch
*Assistant Examiner*—Kahsay Habte
(74) *Attorney, Agent, or Firm*—Jacobson Holman, PLLC

(57) ABSTRACT

N-oxides of formula 1

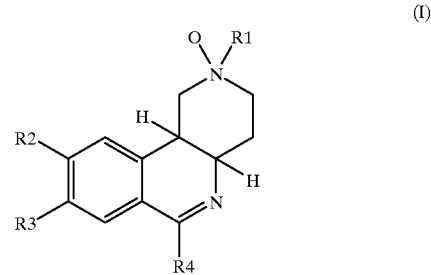

wherein R1, R2, R3 and R4 have the meanings given in the description, are selective inhibitors of types 3 and 4 of cyclic nucleotide phosphodiesterase (PDE3, PDE4); they are useful on the one hand as bronchial therapeutics but on the other hand especially for the treatment of disorders of inflammatory nature.

10 Claims, No Drawings

N-OXIDES

FIELD OF APPLICATION OF THE INVENTION

The invention relates to novel benzonaphthyridine N-oxides which are used in the pharmaceutical industry for the production of medicaments.

KNOWN TECHNICAL BACKGROUND

DE-A 21 23 328 and U.S. Pat. No. 3,899,494 describe substituted benzonapthyridines which are distinguished by marked inhibition of platelet aggregation. EP 247 971 and WO 91/17991 disclose 6-phenyl benzonapthyridines for the treatment of inflammatory airway disorders.

DESCRIPTION OF THE INVENTION

It is has now been found that the compounds of the formula I, which are described in detail below and differ from the compounds of EP 247 971 and WO 91/17991 by the substitution on the 6-phenyl ring and the presence of an N-oxide in the 2-position, have surprisingly and particularly advantageous properties.

Thus, the invention provides compounds of the formula I,

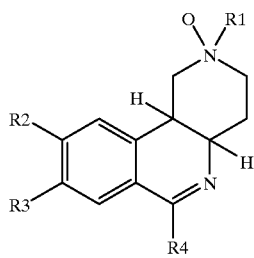

(I)

in which
R1 is 1–4C-alkyl,
R2 is hydroxyl, 1–4C-alkoxy, 3–7C-cycloalkoxy, 3–7C-cycloalkylmethoxy or 1–4C-alkoxy which is completely or predominantly substituted by fluorine,
R3 is hydroxyl, 1–4C-alkoxy, 3–7C-cycloalkoxy, 3–7C-cycloalkylmethoxy or 1–4C-alkoxy which is completely or predominantly substituted by fluorine,
or in which
R2 and R3 together are a 1–2C-alkanedioxy group,
R4 is a phenyl radical which is substituted by R5 and R6, where
R5 is hydrogen, hydroxyl, halogen, nitro, 1–4C-alkyl, trifluoromethyl or 1–4C-alkoxy,
R6 is CO—R7 or CO—R8, where
R7 is hydroxyl, 1–8C-alkoxy, 3–7C-cycloalkoxy or 3–7C-cycloalkylmethoxy and
R8 is N(R81)R82, where R81 and R82 independently of one another are hydrogen, 1–7C-alkyl, 3–7C-cycloalkyl or 3–7C-cycloalkylmethyl, or where R81 and R82, together and including the nitrogen atom to which both are bonded, are a 1-pyrrolidinyl, 1-piperidyl, 1-hexahydroazepinyl or 4-morpholinyl radical,
and to the salts of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3–7C-Cycloalkoxy represents cyclopropyloxy, cyclobutyloxy, cyclopentyloxy, cyclohexyloxy or cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

As 1–4C-Alkoxy which is completely or predominantly substituted by fluorine, the 2,2,3,3,3-pentafluoropropoxy, the perfluoroethoxy, the 1,1,2,2-tetrafluoroethoxy, the 1,2,2-trifluoroethoxy, the trifluoromethoxy, in particular the 2,2,2-trifluoroethoxy, and preferably the difluoromethoxy radicals, for example, may be mentioned.

1–2C-Alkanedioxy represents, for example, the methylenedioxy radical (—O—CH$_2$—O—) or the ethylenedioxy radical (—O—CH$_2$—CH$_2$—O—).

Halogen within the meaning of the invention is fluorine, chlorine or bromine.

1–8C-Alkoxy represents radicals, which, in addition to the oxygen atom, contain a straight-chain or branched alkyl radical having 1 to 8 carbon atoms. Examples which may be mentioned are the octyloxy, heptyloxy, hexyloxy, pentyloxy, methylbutoxy, ethylpropoxy, butoxy, isobutoxy, sec-butoxy, tertbutoxy, propoxy or, preferably, the isopropoxy, ethoxy or methoxy radicals.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl or methyl radicals.

3–7C-Cycloalkyl represents the cyclopropyl, cyclobutyl, cyclopentyl, cyclohexyl or cycloheptyl radicals.

3–7C-Cycloalkylmethyl represents a methyl radical which is substituted by one of the abovementioned 3–7C-cycloalkyl radicals. Examples which may be mentioned are the cycloalkylmethyl radicals cyclopropylmethyl, cyclobutylmethyl and cyclopentylmethyl.

Suitable salts of compounds of the formula I—depending on substitution—are all acid addition salts or all salts with bases. The pharmacologically acceptable salts of the inorganic and organic acids and bases customarily used in pharmacy may be particularly mentioned. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxylbenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand—for example in the case of carboxyl substitution—salts with bases are also suitable. Examples of salts with bases which may be mentioned are alkali metal (lithium, sodium, potassium) or calcium, aluminium, magnesium, titanium, ammonium, meglumine or guanidinium salts, where here too the bases are employed in salt preparation in an equimolar quantitative ratio or one differing therefrom.

Pharmacologically unacceptable salts which can be obtained first, for example, as process products in the preparation of the compounds according to the invention on an industrial scale, are converted into pharmacologically acceptable salts by methods known to the person skilled in the art.

It is known to the person skilled in the art that both the compounds according to the invention and salts thereof may contain various amounts of solvents, for example when they are isolated in crystalline form. Accordingly, the invention also embraces all solvates and in particular all hydrates of the compounds of the formula 1, and all solvates and in particular all hydrates of the salts of the compounds of the formula I.

Compounds of the formula I to be emphasized are those in which

R1 is 1–4C-alkyl,

R2 is 1–4C-alkoxy, 3–7C-cycloalkoxy, 3–7C-cycloalkylmethoxy or 1–2C-alkoxy which is completely or predominantly substituted by fluorine, R3 is 1–4C-alkoxy, 3–7C-cycloalkoxy, 3–7C-cycloalkylmethoxy or 1–2C-alkoxy which is completely or predominantly substituted by fluorine, R4 is a phenyl radical which is substituted by R5 and R6, where R5 is hydrogen, hydroxyl, halogen, nitro, 1–4C-alkyl, trifluoromethyl or 1–4C-alkoxy, R6 is CO—R7 or CO—R8, where R7 is hydroxyl, 1–8C-alkoxy, 3–7C-cycloalkoxy or 3–7C-cycloalkylmethoxy and R8 is N(R81)R82, where R81 and R82 independently of one another are hydrogen, 1–7C-alkyl, 3–7C-cycloalkyl or 3–7C-cycloalkylmethyl, or where R81 and R82, together and including the nitrogen atom to which both are bonded, are a 1-piperidyl, 1-hexahydroazepinyl or 4-morpholinyl radical, and the salts of these compounds.

One embodiment of the compounds of the formula I to be emphasized is those compounds in which R1 is methyl, R2 is 1–4C-alkoxy, R3 is 1–4C-alkoxy, R4 is a phenyl radical which is substituted by R5 and R6, where R5 is hydrogen, hydroxyl, 1–4C-alkyl or 1–4C-alkoxy, R6 is CO—R7 or CO—R8, where R7 hydroxyl, 1–8C-alkoxy or 3–7C-cycloalkoxy and R8 is N(R81)R82, where R81 and R82 independently of one another are hydrogen, 1–7C-alkyl or 3–7C-cycloalkyl, or where R81 and R82, together and including the nitrogen atom to which both are bonded, are a 1-piperidyl, 1-hexahydroazepinyl or 4-morpholinyl radical, and the salts of these compounds.

Compounds of the formula I particularly to be emphasized are those in which

R1 is methyl,

R2 is methoxy, ethoxy or propoxy,

R3 is methoxy or ethoxy,

R4 is a phenyl radical which is substituted by R5 and R6, where

R5 is hydrogen,

R6 is CO—R7 or CO—R8, where

R7 hydroxyl or 1–8C-alkoxy and

R8 is N(R81)R82, where R81 and R82 independently of one another are hydrogen or 1–4C-alkyl or 5–7C-cycloalkyl, or where R81 and R82, together and including the nitrogen atom to which both are bonded, are a 1-piperidyl, 1-hexahydroazepinyl or 4-morpholinyl radical, and the salts of these compounds.

One embodiment of the compounds of the formula I particularly to be emphasized is those compounds in which R1 is methyl, R2 is methoxy or ethoxy, R3 is methoxy or ethoxy, R4 is a phenyl radical which is substituted by R5 and R6, where R5 is hydrogen, R6 is CO—R7 or CO—R8, where R7 is hydroxyl or 1–8C-alkoxy and R8 is N(R81)R82, where R81 and R82 independently of one another are hydrogen or 1–4C-alkyl or 5–7C-cycloalkyl, or where R81 and R82, together and including the nitrogen atom to which both are bonded, are a 1-piperidyl, 1-hexahydroazepinyl or 4-morpholinyl radical, and the salts of these compounds.

Preferred compounds of the formula I are those in which

R1 is methyl,

R2 is ethoxy or propoxy,

R3 is methoxy or ethoxy,

R4 is a phenyl radical which is substituted by R5 and R6, where

R5 is hydrogen,

R6 is CO—R7 or CO—R8, where

R7 is 1–4C-alkoxy and

R8 is N(R81)R82, where R81 and R82 independently of one another are 1–4C-alkyl or 5–7C-cycloalkyl, or where R81 and R82, together and including the nitrogen atom to which both are bonded, are a 1-piperidyl or 1-hexahydroazepinyl radical, and the salts of these compounds.

One embodiment of the preferred compounds of the formula I is those in which

R1 is methyl,

R2 is ethoxy,

R3 is methoxy or ethoxy,

R4 is a phenyl radical which is substituted by R5 and R6, where

R5 is hydrogen,

R6 is CO—R7 or CO—R8, where

R7 is 1–4C-alkoxy and

R8 is N(R81)R82, where R81 and R82 independently of one another are 1–4C-alkyl or 5–7C-cycloalkyl, or where R81 and R82, together and including the nitrogen atom to which both are bonded, are a 1-piperidyl or 1-hexahydroazepinyl radical, and the salts of these compounds.

Particularly preferred compounds of the formula I are those in which

R1 is methyl,
R2 is ethoxy or propoxy,
R3 is methoxy,
R4 is a phenyl radical which is substituted by R5 and R6, where
R5 is hydrogen,
R6 is CO—R8, where
R8 is N(R81)R82, where R81 and R82 independently of one another are 1–4C-alkyl,
and the salts of these compounds.

The compounds of the formula I are chiral compounds having chiral centres in positions 2, 4a and 10b Numbering:

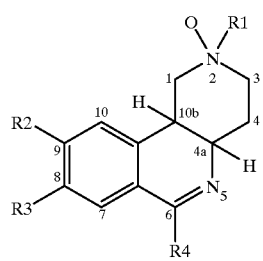
(I)

The invention provides all eight conceivable diastereomers in any mixing ratio. Preference is given to the compounds of the formula I in which the hydrogen atoms in positions 4a and 10b are in the cis position relative to one another.

Particularly preferred in this context are those compounds of the formula I which in positions 4a and 10b have the same absolute configuration as the compound (-)-cis-4-amino-3-(3-ethoxy-4-methoxyphenyl)-1-methylpiperidine dihydrochloride having the optical rotation $[\alpha]_D^{20}=-65.5°$ (c=1, methanol) which can be employed as starting material.

The invention further provides a process for preparing the compounds of the formula I in which R1, R2, R3 and R4 have the meanings indicated above, and salts thereof. The process comprises subjecting compounds of the formula II

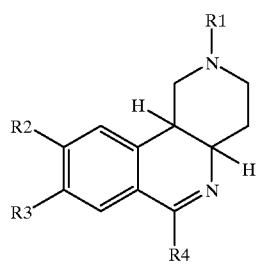
(II)

in which R1, R2, R3 and R4 have the meanings indicated above to an N-oxidation and, if desired, then converting the resulting compounds of the formula I into their salts, or, if desired, then converting the resulting salts of the compound s of the formula I into free compounds.

The N-oxidation is carried out in a manner familiar to the person skilled in the art, for example with the aid of hydrogen peroxide in methanol or with the aid of m-chloroperoxibenzoic acid in dichloromethane at room temperature. The reaction conditions specifically required for carrying out the process are known to the person skilled in the art owing to his expert knowledge.

If desired, compounds of the formula I obtained can be converted into further compounds of the formula I by derivatization. For example, the corresponding acids can be obtained from compounds of the formula I in which R4 is a phenyl radical which is substituted by R5 and R6, and R6 is an ester group, by acidic or alkaline hydrolysis, or the corresponding amides can be prepared by reaction with amines of the formula HN(R81)R82 in which R81 and R82 have the meanings indicated above. The reactions are expediently carried out analogously to methods known to the person skilled in the art.

Compounds of the formula II in which R1, R2, R3 and R4 have the meanings indicated above can be prepared from the corresponding compounds of the formula III

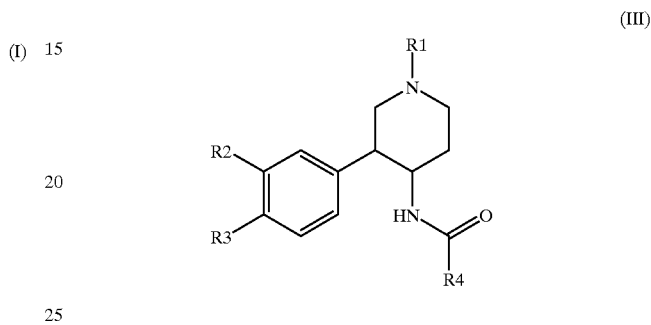
(III)

in which R1, R2, R3 and R4 have the meanings indicated above, by a cyclocondensation reaction.

The cyclocondensation is likewise carried out in a manner known to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus trichloride, phosphorus pentoxide, thionyl chloride or preferably phosphorus oxytrichloride, in a suitable inert solvent, e.g. in a chlorinated hydrocarbon such as chloroform, or in a cyclic hydrocarbon such as toluene or xylene, or another inert solvent such as acetonitrile, or without a further solvent using an excess of condensing agent, preferably at elevated temperature, in particular at the boiling point of the solvent or condensing agent used.

Enantiomerically pure compounds of the formula II can be separated in a known manner (for example by preparing and separating corresponding diastereomeric compounds) or be prepared by stereo selective synthesis methods. Such separation processes and synthesis methods are described, for example, in EP 247 971 and in DE 42 17 401.

Compounds of the formula III in which R1, R2, R3 and R4 have the meanings indicated above are accessible from the corresponding compounds of the formula IV,

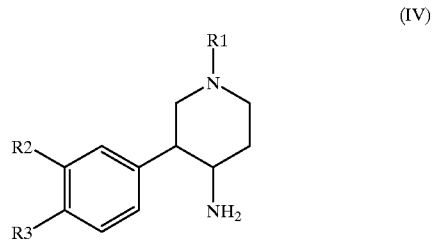
(IV)

in which R1, R2 and R3 have the meanings indicated above, by reaction with compounds of the formula R4—CO—X, in which R4 has the meaning indicated above and X is a suitable leaving group, preferably a chlorine atom. For example, the benzoylation is carried out as in the following examples according to the Einhorn process, the Schotten-Baumann variant or as described in J. Chem. Soc. (C), 1971, 1805–1808.

The preparation of cis-/trans-racemate mixtures and of pure cis-racemate of compounds of the formula IV is described, for example, in U.S. Pat. No. 3,899,494, in DE-A 21 23 328 and in DE-A 16 95 782. Pure cis-enantiomers of the compounds of the formula IV can be obtained, for example, by the processes as are disclosed in EP 0 247 971 and in DE 42 17 401.

Compounds of the formula R4—CO—X are either known or can be prepared in a known manner.

The substances according to the invention are isolated and purified in a manner known per se, for example by distilling off the solvent in vacuo and recrystallizing the residue obtained from a suitable solvent or subjecting it to one of the customary purification methods, such as, for example, column chromatography on a suitable support material.

Salts are obtained by dissolving the free compound in a suitable solvent (for example a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol), which contains the desired acid or base or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

The following examples serve to illustrate the invention in greater detail without restricting it. Further compounds of the formula I, whose preparation is not explicitly described, can also be prepared in an analogous manner or in a manner familiar per se to the person skilled in the art using customary procedures.

In the examples, m.p. denotes melting point, h denotes hour(s), RT denotes room temperature, EF denotes empirical formula, MW denotes molecular weight, calc. denotes calculated. The compounds mentioned in the examples and their salts are a preferred subject of the invention.

EXAMPLES

Final Products 1. cis-9-ethoxy-8-methoxy-2-methyl-6-(4-diisopropylaminocarbonylphenyl)-1,2,3,4,4a,10b-hexahydrobenzo[c][1,6]naphthyridine N-2-oxide A solution of 5.0 g of (-)cis-9-ethoxy-8-methoxy-6-(4-diisopropylaminocarbonylphenyl)-2-methyl-1,2,3,4,4a,10b-hexahydrobenzo[c][1,6]naphthyridine in 40 ml of methanol is stirred at RT with 6 ml of 30% hydrogen peroxide for about 2 days. After the oxidation is complete (TLC control), the reaction mixture is admixed with 7 g of solid sodium sulphite and stirred at RT for about another 1 h. The reaction mixture is filtered off with suction, the filtrate is then extracted with dichloromethane and the organic phase is washed with saturated sodium bicarbonate solution and then with water and dried over sodium sulphate. The product solution is filtered off with suction and concentrated, and the resulting solid residue is recrystallized in an acetone/ethyl acetate mixture (10+1). This gives 2.7 g of the title compound as fine colourless crystals of m.p. 195–198° C.
EF: $C_{29}H_{39}N_3O_4 \times 1.38\ H_2O$; MW: 518.52

| Elemental analysis: | calc.: C 67.19 H 8.12 N 8.11 |
| --- | --- |
| | found: C 67.18 H 8.00 N 8.13 |

Starting from the corresponding starting materials, the two final products below are prepared analogously to Example 1:

2. cis-9-ethoxy-2-methyl-8-methoxy-6-(4-dibutylaminocarbonylphenyl)-1,2,3,4,4a,10b-hexahydrobenzo[c][1,6]naphthyridine N-2-oxide
EF: $C_{31}H_{43}N_3O_4$; MW: 521.7; m.p. 66–80° C. (slow deliquescence), above 80° C. decomposition.

3. cis-8-methoxy-2-methyl-9-propoxy-6-(4-dibutylaminocarbonylphenyl)-1,2,3,4,4a,10b-hexahydrobenzo[c][1,6]naphthyridine N-2-oxide
EF: $C_{32}H_{45}N_3O_4$; MW: 535.7; m.p. 104–1 08° C. (slow deliquescence), above 108° C. decompositon.

Starting Materials

A1. (-)-cis-9-ethoxy-8-methoxy-6-(4-diisopropylaminocarbonylphenyl)-2-methyl-1,2,3,4,4a,10b-hexahydrobenzo[c][1,6]naphthyridine hydrochloride 6.36 g of (-)-cis-terephthalic acid N,N-diisopropyl-N'-[3-(3-ethoxy-4-methoxyphenyl)-1-methylpiperidin-4-yl] diamide in 100 ml of acetonitrile and 12 ml of phosphorus oxytrichloride are heated at the boil under reflux for 15 h. Excess phosphorus oxytrichloride is distilled off and the residue is then partitioned between dichloromethane and saturated sodium bicarbonate solution. The organic phase is washed with water, dried over sodium sulphate and concentrated. The solid residue is purified by silica gel chromatography and the main product fraction is separated off and concentrated. The solid residue is dissolved in a little methanol and the solution is admixed with 1 equivalent of aqueous HCl and concentrated. The solid residue is recrystallized in methanol/diethyl ether. This gives 4.51 g of the title compound as hydrochloride 0.6-hydrate of m.p. 175–179° C. (unsharp).
EF: $C_{29}H_{39}N_3O_3 \times HCl \times 0.6\ H_2O$; MW: 524.92

| Elemental analysis: | calc.: C 66.36 H 7.91 Cl 6.75 N 8.01 |
| --- | --- |
| | found: C 66.28 H 7.99 Cl 6.87 N 7.97 |
| Optical rotation: | $[\alpha]_D^{20} = -42.7°$ (c = 1, methanol). |

The free base is obtained from the hydrochloride by extraction with dichloromethane after treatment with dilute aqueous sodium hydroxide solution.

Starting from the corresponding starting materials, A2 and A3 are prepared analogously to Example A1.

A2. (-)-cis-9-ethoxy-8-methoxy-2-methyl-6-(4-dibutylaminocarbonylphenyl)-,2,3,4,4a,10b-hexahydrobenzo[c][1,6]naphthyridine hydrochloride
EF: $C_{31}H_{43}N_3O_3 \times 1.1\ HCl \times 1.17\ H_2O$; MW: 566.82; m.p.: 104–112° C. (solid foamed product, slow deliquescence);

| Elemental analysis: | calc.: C 65.68 H 8.26 Cl 6.88 N 7.41 |
| --- | --- |
| | found: C 65.80 H 8.09 Cl 6.97 N 7.49 |

Optical rotation: $[\alpha]_D^{20} = -16.2°$ (c=1, methanol).

A3. (-)-cis-8-methoxy-2-methyl-9-propoxy-6-(4-dibutylaminocarbonylphenyl)-,2,3,4,4a,10b-hexahydrobenzo[c][1,6]naphthyridine hydrochloride
EF: $C_{32}H_{45}N_3O_3 \times 1.05$ HCl$\times 0.58$ H$_2$O; MW: 568.5; m.p. 105–112°C. (unsharp);

| Elemental analysis: | calc.: C 67.64 H 8.37 Cl 6.55 N 7.39 |
| --- | --- |
| | found: C 67.55 H 8.29 Cl 6.68 N 7.31 |
| Optical rotation: | $[\alpha]_D^{20} = -15.8°$ (c = 1, methanol). |

B1. (-)-cis-Terephthalic acid N,N-diisopropyl-N'-[3-(3-ethoxy-4-methoxyphenyl)-1-methylpiperidin4-yl]diamide At room temperature, a solution of 4-diisopropylaminocarbonylbenzoyl chloride (prepared from 1.5 g of 4-diisopropylaminocarbonylbenzoic acid and thionyl chloride) in 60 ml of dichloromethane is added dropwise over a period of 10 min. to a solution of 1.5 g of (-)-cis-4-amino-3-(3-ethoxy-4-methoxyphenyl)-1-methylpiperidine [prepared by extraction of the free base with dichloromethane following treatment of the corresponding dihydrochloride ($[\alpha]_D^{20}=-65.5°$, c=1, methanol) with dilute aqueous sodium hydroxide solution] in 60 ml of dichloromethane in 0.9 ml of triethylamine. After about 2 h of stirring, the mixture is extracted with about 50 ml of saturated sodium bicarbonate solution and the organic phase is washed twice with in each case 50 ml of water and dried over sodium sulphate. The highly viscous residue that remains after concentration is purified by column chromatography. The main product fraction is concentrated under reduced pressure, giving a solid foaming residue which is recrystallized in the mixture of methanol and diethyl ether (about 1+1 by volume). This gives 2.7 g of the title compound of m.p. 75–82° C. (unsharp range, solidified foam).
EF: $C_{29}H_{41}N_3O_4$; MW: 495.67
Optical rotation: $[\alpha]_D^{20}=-60.1°$ (c=1, methanol).

The compound below is obtained analogously to the process described in DE 42 17 401 by employing, in the examples described therein, the 3-ethoxy-4-methoxy compounds instead of the 3,4-dimethoxy compounds:

C1. (-)-cis-4-amino-3-(3-ethoxy-4-methoxyphenyl)-1-methylpiperidine dihydrochloride
EF: $C_{15}H_{24}N_2O_2 \times 2$ HCl$\times 0.96$ H$_2$O; MW: 354.52; m.p.: 252–254° C.;
Optical rotation: $[\alpha]_D^{20}=-65.5°$ (c=1, methanol).

Commercial Utility

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating action and cilia-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumor necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherent proteins (e.g. integrins). The compounds according to the invention have smooth muscle-relaxant action, e.g. in the region of the bronchial system, of the blood circulation, and of the efferent urinary passages. Furthermore, they have cilia frequency-increasing action, for example in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origin (bronchitis, allergic bronchitis, bronchial asthma, emphysema, COPD); disorders associated with impaired cilia function or increased demands on ciliar clearance (bronchitis, mucoviscidosis dermatoses (especially of proliferative, inflammatory and allergic type) such as, for example, psoriasis (vulgaris), toxic and allergic contact eczema, atopic eczema, seborrheic eczema, lichen simplex, sunburn, pruritis in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (type 1, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origin such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as antithrombotic, platelet aggregation-inhibiting substances.

The invention further relates to a method for the treatment of mammals including humans who are suffering from one of the abovementioned diseases. The method comprises administering a therapeutically effective and pharmacologically acceptable amount of one or more of the compounds according to the invention to the sick mammal.

The invention further relates to the compounds according to the invention for use in the treatment and/or prophylaxis of diseases, in particular the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned and which contain one or more of the compounds according to the invention.

A further subject of the invention is a commercial product, consisting of a customary secondary pack, a primary pack containing the medicament (for example an ampoule or a blister pack) and, if desired, an information leaflet, the medicament exhibiting antagonistic action against cyclic nucleotide phosphodiesterases of type 3 and 4 and leading to the attenuation of the symptoms of illnesses which are connected with cyclic nucleotide phosphodiesterases of type 3 and 4, and the suitability of the medicament for the prophylaxis or treatment of illnesses which are connected with cyclic nucleotide phosphodiesterases of type 3 and 4 being indicated on the secondary pack and/or on the information leaflet of the commercial product, and the medicament containing one or more compounds of the formula I according to the invention. The secondary pack, the primary pack containing the medicament and the information leaflet otherwise comply with what would be regarded as standard to the person skilled in the art for medicaments of this type.

Advantageously, the substances according to the invention are also suitable for combination with other substances which bring about stimulation of cAMP, such as prostaglandins (PGE2, PGI2 and prostacyclin) and their derivatives, direct adenylate cyclase stimulators such as forskolin and related substances, or substances indirectly stimulating adenylate cyclase, such as catecholamines and adrenergic receptor agonists, in particular beta mimetics. In combination, on account of their cAMP degradation-inhibiting action, they in this case display a synergistic, superadditive activity. This comes to bear, for example, in their use in combination with PGE2 for the treatment of pulmonary hypertension.

The medicaments are prepared by methods known per se familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointment bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are administered either directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the invention are used in particular in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.01 and 10 mg per kilogram per day.

Biological Investigations

In the investigation of PDE4 inhibition at the cellular level, the activation of inflammatory cells has particular importance. An example which may be mentioned is the FMLP (N-formylmethionylleucylphenylalanine)-induced superoxide production of neutrophilic granulocytes, which can be measured as luminol-potentiated chemoluminescence [McPhail LC, Strum SL, Leone PA and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemoluminescence and cytokine secretion and the secretion of inflammation-increasing mediators in inflammatory cells, in particular neutrophilic and eosinophilic granulocytes, T-lymphocytes, monocytes and macrophages are those which inhibit PDE4 or PDE3 and PDE 4. The last-mentioned isoenzyme of the phosphodiesterase families is particularly represented in granulocytes. Its inhibition leads to an increase in the intracellular cyclic AMP concentration and thus to the inhibition of cellular activation. PDE4 inhibition by the substances according to the invention is thus a central indicator of the suppression of inflammatory processes. (Giembycz Mass., Could isoenzyme-selective phosphodiesterase inhibitors render bronchodilatory therapy redundant in the treatment of bronchial asthma?; Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE3/4 inhibitor. In "New Drugs for Asthma Therapy", 379–402, Birkhauser Verlag Basel 1991; Schudt C et al., Influence of selective phosphodiesterase inhibitors on human neutrophil functions and levels of cAMP and Ca. Naunyn-Schmiedebergs Arch Pharmacol. 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press 1996. Hatzelmann A et al., Enzymatic and functional aspects of dual-selective PDE3/4-inhibitors. In "Phosphodiesterase Inhibitors", 147–160, "The Handbook of Immunopharmacology", Academic Press, 1996.

A. Methodology

1. Inhibition of PDE isoenzymes

The PDE activity was determined according to Thompson et al. (1) with some modifications (2). The test samples contained 40 mM tris HCl (pH 7.4), 5 mM $MgCl_2$, 0.5 µM cAMP or cGMP, [$^3$H] cAMP or [3H]CGMP (about 50,000 cpm/sample), the PDE isoenzyme-specific additions described in greater detail below, the indicated concentrations of inhibitor and an aliquot of the enzyme solution in a total sample volume of 200 µl. Stock solutions of the compounds to be investigated in DMSO were prepared in concentrations such that the DMSO content in the test samples did not exceed 1% by volume—to avoid an effect on the PDE activity. After preincubation at 37° C. for 5 minutes, the reaction was started by addition of the substrate (cAMP or cGMP). The samples were incubated at 37° C. for a further 15 min. The reaction was terminated by addition of 50 µl of 0.2 N HCl. After cooling on ice for 10 minutes and addition of 25 µg of 5'-nucleotidase (snake venom from Crotalus atrox), the mixture was again incubated at 37° C. for 10 min and the samples were then applied to QAE Sephadex A-25 columns. The columns were eluted with 2 ml of 30 mM ammonium formate (pH 6.0). The radioactivity of the eluate was measured and corrected by the corresponding blank values. The proportion of hydrolysed nucleotide in no case exceeded 20% of the original substrate concentration.

PDE1 ($Ca^{2+}$/calmodulin-dependent) from bovine brain: the inhibition of this isoenzyme was investigated in the presence of $Ca^{2+}$ (1 mM) and calmodulin (100 nM) using cGMP as a substrate (3).

PDE2 (cGMP-stimulated) from rat hearts was purified chromatographically [Schudt et al. (4)] and investigated in the presence of cGMP (5 µM) using cAMP as a substrate.

PDE3 (cGMP-inhibited) and PDE5 (cGMP-specific) were investigated in homogenates of human blood platelets [Schudt et al. (4)] using cAMP or cGMP as a substrate.

PDE4 (cAMP-specific) was investigated in the cytosol of human polymorphonuclear leukocytes (PMNL) [isolated from leukocyte concentrates, see Schudt et al. (5)] using cAMP as a substrate. The PDE3 inhibitor motapizone (1 µM) was used in order to suppress the PDE3 activity emanating from contaminating blood platelets.

2. Statistics

The $IC_{50}$ values were determined from the concentration-inhibition curves by nonlinear regression using the Graph-Pad InPlot™ program (GraphPad Software Inc., Philadelphia, USA).

3. References
(1) Thompson W. J. and Terasaki W. L., Epstein P. M. and Strada S. J., Assay of cyclic nucleotide phosphodiesterase and resolution of multiple molecular forms of the enzyme; Adv. Cycl. Nucl. Res. 1979,10, 69–92
(2) Bauer A. C. and Schwabe U., An improved assay of cyclic 3',5'-nucleotide phosphodiesterase with QAE Sephadex A-25; Naunyn-Schmiedeberg's Arch. Pharmacol. 1980, 311, 193–198
(3) Gietzen K., Sadorf I. and Bader H., A model for the regulation of the calmodulin-dependent enzymes erythrocyte $Ca^{2+}$-transport ATPase and brain phosphodiesterase by activators and inhibitors; Biochem. J. 1982, 207, 541–548.
(4) Schudt C., Winder S., Müller B. and Ukena D., Zardaverine as a selective inhibitor of phosphodiesterase isoenzymes; Biochem. Pharmacol. 1991, 42, 153–162
(5) Schudt C., Winder S., Forderkunz S., Hatzelmann A. and Ullrich V., Influence of selective phosphodiesterase inhibitors on human neutrophil functions and levels of cAMP and Ca; Naunyn-Schmiedeberg's Arch. Pharmacol. 1991, 344, 682–690

B. Results

In Table 1 below, the inhibitory concentrations determined according to Section A1 [inhibitory concentrations as -log $IC_{50}$ (mol/l)] are indicated for some compounds according to the invention. The numbers of the compounds correspond to the numbers of the examples.

TABLE 1

| Compound | PDE4 [-logl$C_{50}$,mol/l] | PDE3 |
|---|---|---|
| 1 | 7.20 | 6.11 |
| 2 | 7.98 | 5.97 |
| 3 | 7.53 | 5.68 |

What is claimed is:
1. A compound of formula 1

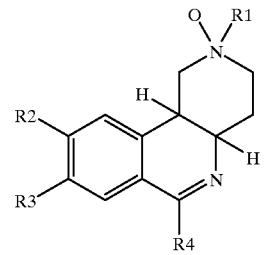

(I)

in which

R1 is 1–4C-alkyl,

R2 is hydroxyl, 1–4C-alkoxy, 3–7C-cycloalkoxy, 3–7C-cycloalkylmethoxy or 1–4C-alkoxy in which the hydrogen atoms are completely or predominantly replaced by fluorine, R3 is hydroxyl, 1–4C-alkoxy, 3–7C-cycloalkoxy, 3–7C-cycloalkymethoxy or 1–4C-alkoxy in which the hydrogen atoms are completely or predominantly replaced by fluorine, or in which R2 and R3 together are a 1–2C-alkanedioxy group, R4 is a phenyl radical which is substituted by R5 and R6, where R5 is hydrogen, hydroxyl, halogen, nitro, 1–4C-alkyl, trifluoromethyl or 1–4C-alkoxy, R6 is CO—R7 or CO—R8, where R7 is hydroxyl, 1–8C-alkoxy, 3–7C-cycloalkoxy or 3–7C-cycloalkylmethoxy and R8 is N(R81)R82, where R81 and R82 independently of one another are hydrogen, 1–7C-alkyl, 3–7C-cycloalkyl or 3–7C-cycloalkylmethyl, or where R81 and R82, together and including the nitrogen atom to which both are bonded, are a 1-pyrrolidinyl, 1-piperidyl, 1-hexahydroazepinyl or 4-morpholinyl radical, or a salt thereof.

2. A compound of formula 1 according to claim 1 in which

R1 is methyl,

R2 is 1–4C alkoxy,

R3 is 1–4C-alkoxy,

R4 is a phenyl radical which is substituted by R5 and R6, where

R5 is hydrogen, hydroxyl, 1–4C-alkyl or 1–4C-alkoxy,

R6 is CO—R7 or CO—R8, where

R7 hydroxyl, 1–8C-alkoxy or 3–7C-cycloalkoxy and

R8 is N(R81)R82, where R81 and R82 independently of one another are hydrogen, 1–7C-alkyl or 3–7C-cycloalkyl, or where R81 and R82, together and including the nitrogen atom to which both are bonded, are a 1-piperidyl, 1-hexahydroazepinyl or 4-morpholinyl radical, or a salt thereof.

3. A compound of formula 1 according to claim 1 in which

R1 is methyl

R2 is methoxy, ethoxy or propoxy,

R3 is methoxy or ethoxy,

R4 is a phenyl radical which is substituted by R5 and R6, where

R5 is hydrogen

R6 is CO—R7 or CO—R8, where

R7 is hydroxyl or 1–8C-alkoxy and

R8 is N(R81)R82, where R81 and R82 independently of one another are hydrogen or 1–4C-alkyl or 5–7C-cycloalkyl, or where R81 and R82, together and including the nitrogen atom to which both are bonded, are a 1-piperidyl, 1-hexahydroazepinyl or 4-morpholinyl radical, or a salt thereof.

4. A compound of formula 1 according to claim 1 in which

R1 is methyl,

R2 is ethoxy,

R3 is methoxy or ethoxy,

R4 is a phenyl radical which is substituted by R5 and R6, where

R5 is hydrogen,

R6 is CO—R7 or CO—R8, where

R7 is 1–4C-alkoxy and

R8 is N(R81)R82, where R81 and R82 independently of one another are 1–4C-alkyl or 5–7C-cycloalkyl, or where R81 and R82, together and including the nitrogen atom to which both are bonded are a 1-piperidyl or 1-hexahydroazepinyl radical, or a salt thereof.

5. A compound of formula 1 according to claim 1 in which

R1 is methyl,

R2 is ethoxy or propoxy,

R3 is methoxy,

R4 is a phenyl radical which is substituted by R5 and R6, where

R5 is hydrogen,

R6 is CO—R8, where

R8 is N(R81)R82, where R81 and R82 independently of one another are 1–4C-alkyl, or a salt thereof.

6. A compound of formula 1 according to claim 1 in which the hydrogen atoms in positions 4a and 10b are in the cis position relative to one another.

7. A compound of formula 1 according to claim 1 which, in positions 4a and 10b, have the same absolute configuration as the compound (−)-cis-4-amino-3-(3-ethoxy-4-methoxyphenyl)-1-methylpiperidine dihydrocholoride having the optional rotation $[\alpha]_D^{20}=-65.5$ (c=1, methanol).

8. A method of treating a subject afflicted with a condition amenable to treatment with a selective inhibitor of types 3 and 4 of cyclic nucleotide phosphodiesterase, which comprises administering to the subject an effective amount of a compound as claimed in claim 1 or of a pharmaceutically acceptable salt thereof.

9. A medicament composition containing a pharmaceutical auxiliary and/or carrier material and a compound according to claim 1 or a pharmaceutically acceptable salt thereof.

10. A method of compounding a medicament composition for treating an airway disorder and/or a dermatosis by combining a pharmaceutical auxiliary and/or carrier material with a PDE-inhibitor, wherein the PDE-inhibitor is a compound according to claim 1 or a pharmaceutically acceptable salt thereof.

* * * * *